(12) United States Patent
Maschino

(10) Patent No.: US 8,972,013 B2
(45) Date of Patent: Mar. 3, 2015

(54) USING PHYSIOLOGICAL SENSOR DATA WITH AN IMPLANTABLE MEDICAL DEVICE

(75) Inventor: Steven E. Maschino, Seabrook, TX (US)

(73) Assignee: Cyberonics, Inc., Houston, TX (US)

(*) Notice: Subject to any disclaimer, the term of this patent is extended or adjusted under 35 U.S.C. 154(b) by 201 days.

(21) Appl. No.: 13/072,430

(22) Filed: Mar. 25, 2011

(65) Prior Publication Data

US 2011/0172732 A1 Jul. 14, 2011

Related U.S. Application Data

(62) Division of application No. 11/261,853, filed on Oct. 28, 2005, now Pat. No. 7,957,796.

(51) Int. Cl.
*A61N 1/36* (2006.01)
*A61N 1/32* (2006.01)
*A61N 1/362* (2006.01)

(52) U.S. Cl.
CPC .............. *A61N 1/32* (2013.01); *A61N 1/36135* (2013.01); *A61N 1/36053* (2013.01); *A61N 1/36064* (2013.01); *A61N 1/36082* (2013.01); *A61N 1/3627* (2013.01)
USPC ........ 607/40; 607/9; 607/17; 607/22; 607/45; 607/115; 607/116; 607/117; 607/118; 607/119; 607/133

(58) Field of Classification Search
USPC ............. 607/1–2, 9, 17, 22, 40, 45, 115–119, 607/133; 600/300–301, 508–509
IPC ........ A61N 1/36,1/32, 1/08, 1/306, 1/05; A61M 2205/054; A61B 5/00, 5/4094, 5/4848, 5/7264
See application file for complete search history.

(56) References Cited

U.S. PATENT DOCUMENTS 4,291,699 A 9/1981 Geddes et al.
4,573,481 A 3/1986 Bullara
(Continued)

FOREIGN PATENT DOCUMENTS

EP 1145736 A2 4/2001

OTHER PUBLICATIONS

King, Michael A. et al. "Effects of Short-Term Vagus Nerve Stimulation (VNS) on FOS Expression in Rat Brain Nuclei," 58th Annual Scientific Convention of the Society of Biological Psychiatry, dated May 5-17, 2003, San Francisco, California, 1 page.
(Continued)

*Primary Examiner* — Deborah Malamud
(74) *Attorney, Agent, or Firm* — Cyberonics, Inc.

(57) ABSTRACT

An implantable medical system includes an implantable medical device (IMD) and an electrode coupleable to the IMD. The electrode is operative to deliver a first electrical signal from the IMD to a neural structure. The system includes a sensor coupleable to the IMD. The sensor is operative to sense a physiological parameter. The physiological parameter may include at least one of a neurotransmitter parameter, a neurotransmitter breakdown product parameter, a neuropeptide parameter, a norepinephrine parameter, a glucocorticoid (GC) parameter, a neuromodulator parameter, a neuromodulator breakdown product parameter, an amino acid parameter, and a hormone parameter. The IMD includes a controller operative to change a parameter of the first electrical signal based upon at least one sensed physiological parameter to generate a second electrical signal and to apply the second electrical signal to the neural structure.

18 Claims, 10 Drawing Sheets

(56) References Cited

U.S. PATENT DOCUMENTS

| | | |
|---|---|---|
| 4,702,254 A | 10/1987 | Zabara |
| 4,867,164 A | 9/1989 | Zabara |
| 4,873,655 A | 10/1989 | Kondraske |
| 4,958,632 A | 9/1990 | Duggan |
| 5,025,807 A | 6/1991 | Zabara |
| 5,081,987 A | 1/1992 | Nigam |
| 5,111,815 A | 5/1992 | Mower |
| 5,154,172 A | 10/1992 | Terry, Jr. et al. |
| 5,188,104 A | 2/1993 | Wernicke et al. |
| 5,201,808 A | 4/1993 | Steinhaus et al. |
| 5,203,326 A | 4/1993 | Collins |
| 5,205,285 A | 4/1993 | Baker, Jr. |
| 5,215,086 A | 6/1993 | Terry, Jr. et al. |
| 5,231,988 A | 8/1993 | Wernicke et al. |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,311,876 A | 5/1994 | Olsen et al. |
| 5,501,702 A | 3/1996 | Plicchi et al. |
| 5,569,186 A | 10/1996 | Lord et al. |
| 5,645,570 A | 7/1997 | Corbucci |
| 5,658,318 A | 8/1997 | Stroetmann et al. |
| 5,690,688 A | 11/1997 | Noren et al. |
| 5,702,429 A | 12/1997 | King |
| 5,814,092 A | 9/1998 | King |
| 5,861,014 A | 1/1999 | Familoni |
| 5,913,882 A | 6/1999 | King |
| 5,916,239 A | 6/1999 | Geddes et al. |
| 5,928,272 A | 7/1999 | Adkins et al. |
| 5,987,352 A | 11/1999 | Klein et al. |
| 5,995,868 A | 11/1999 | Dorfmeister et al. |
| 6,018,682 A | 1/2000 | Rise |
| 6,061,593 A | 5/2000 | Fischell et al. |
| 6,083,249 A | 7/2000 | Familoni |
| 6,134,474 A | 10/2000 | Fischell et al. |
| 6,141,590 A | 10/2000 | Renirie et al. |
| 6,167,311 A | 12/2000 | Rezai |
| 6,208,894 B1 | 3/2001 | Schulman et al. |
| 6,248,080 B1 | 6/2001 | Miesel et al. |
| 6,304,775 B1 | 10/2001 | Iasemidis et al. |
| 6,308,102 B1 | 10/2001 | Sieracki et al. |
| 6,327,503 B1 | 12/2001 | Familoni |
| 6,337,997 B1 | 1/2002 | Rise |
| 6,341,236 B1 | 1/2002 | Osorio et al. |
| 6,366,813 B1 | 4/2002 | DiLorenzo |
| 6,381,496 B1 | 4/2002 | Meadows et al. |
| 6,397,100 B2 | 5/2002 | Stadler et al. |
| 6,405,732 B1 | 6/2002 | Edwards et al. |
| 6,459,936 B2 | 10/2002 | Fischell et al. |
| 6,463,328 B1 | 10/2002 | John |
| 6,466,822 B1 | 10/2002 | Pless |
| 6,473,639 B1 | 10/2002 | Fischell et al. |
| 6,473,653 B1 | 10/2002 | Schallhorn et al. |
| 6,477,417 B1 | 11/2002 | Levine |
| 6,477,418 B2 | 11/2002 | Plicchi et al. |
| 6,480,743 B1 | 11/2002 | Kirkpatrick et al. |
| 6,522,928 B2 | 2/2003 | Whitehurst et al. |
| 6,549,804 B1 | 4/2003 | Osorio et al. |
| 6,587,719 B1 | 7/2003 | Barrett et al. |
| 6,587,727 B2 | 7/2003 | Osorio et al. |
| 6,594,524 B2 | 7/2003 | Esteller et al. |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,625,492 B2 | 9/2003 | Florio et al. |
| 6,628,987 B1 | 9/2003 | Hill et al. |
| 6,647,296 B2 | 11/2003 | Fischell et al. |
| 6,671,547 B2 | 12/2003 | Lyster et al. |
| 6,671,555 B2 | 12/2003 | Gielen et al. |
| 6,671,556 B2 | 12/2003 | Osorio et al. |
| 6,684,104 B2 | 1/2004 | Gordon et al. |
| 6,684,105 B2 | 1/2004 | Cohen et al. |
| 6,721,603 B2 | 4/2004 | Zabara et al. |
| 6,768,969 B1 | 7/2004 | Nikitin et al. |
| 6,801,805 B2 | 10/2004 | Stokes et al. |
| 6,819,953 B2 | 11/2004 | Yonce et al. |
| 6,819,956 B2 | 11/2004 | DiLorenzo |
| 6,832,114 B1 | 12/2004 | Whitehurst et al. |
| 6,836,685 B1 | 12/2004 | Fitz |
| 6,853,862 B1 | 2/2005 | Marchal et al. |
| 6,885,888 B2 | 4/2005 | Rezai |
| 6,889,076 B2 | 5/2005 | Cigaina |
| 6,920,357 B2 | 7/2005 | Osorio et al. |
| 6,922,590 B1 * | 7/2005 | Whitehurst ............... 607/45 |
| 6,944,501 B1 | 9/2005 | Pless |
| 6,961,618 B2 | 11/2005 | Osorio et al. |
| 7,006,872 B2 | 2/2006 | Gielen et al. |
| 7,050,856 B2 | 5/2006 | Stypulkowski |
| 2002/0143368 A1 | 10/2002 | Bakels et al. |
| 2002/0151939 A1 | 10/2002 | Rezai |
| 2003/0236558 A1 | 12/2003 | Whitehurst et al. |
| 2004/0153129 A1 | 8/2004 | Pless et al. |
| 2004/0167583 A1 | 8/2004 | Knudson et al. |
| 2004/0172085 A1 | 9/2004 | Knudson et al. |
| 2004/0172091 A1 | 9/2004 | Rezai |
| 2004/0172094 A1 | 9/2004 | Cohen et al. |
| 2004/0176812 A1 | 9/2004 | Knudson et al. |
| 2004/0193231 A1 | 9/2004 | David et al. |
| 2004/0210274 A1 | 10/2004 | Bauhahn et al. |
| 2004/0249416 A1 | 12/2004 | Yun et al. |
| 2005/0021092 A1 | 1/2005 | Yun et al. |
| 2005/0021103 A1 | 1/2005 | DiLorenzo |
| 2005/0021104 A1 | 1/2005 | DiLorenzo |
| 2005/0060010 A1 | 3/2005 | Goetz |
| 2005/0065562 A1 | 3/2005 | Rezai |
| 2005/0065573 A1 | 3/2005 | Rezai |
| 2005/0065575 A1 | 3/2005 | Dobak |
| 2005/0119703 A1 | 6/2005 | DiLorenzo |
| 2005/0131485 A1 | 6/2005 | Knudson et al. |
| 2005/0131506 A1 | 6/2005 | Rezai et al. |
| 2005/0153885 A1 | 7/2005 | Yun et al. |
| 2006/0009815 A1 | 1/2006 | Boveja et al. |
| 2006/0079936 A1 | 4/2006 | Boveja et al. |
| 2006/0095081 A1 | 5/2006 | Zhou et al. |

OTHER PUBLICATIONS

Koo, Betty. "EEG Changes with Vagus Nerve Stimulation," Reprinted from Journal of Clinical Neurophysiology, vol. 18, No. 5, dated Sep. 2001, Lippincott Williams & Wilkins, USA, pp. 434-441.
Ritter, Sue et al. "Neuroanatomy and Physiology of Abdominal Vagal Afferents," R.C. Rogers et al.—Central Regulation of Brainstem Gastric Vago-Vagal Control Circuits, Chapter 5, dated 1992, CRC Press, Inc., USA, 38 pages.
Henry, Thomas R. et al. "Brain Blood Flow Alterations Induced by Therapeutic Vagus Nerve Stimulation in Partial Eplilepsy: I. Acute Effects at High and Low Levels of Stimulation," Epilepsia, vol. 39, No. 9, dated 1998, Lippincott Williams & Wilkins, Philadelphia, pp. 983-990.
Sheikh, S. et al. "Effects of Vagus Nerve Stimulation Therapy on Brain Metablosim in Severe, Chronic, Treatment-Resistant Depression: One-Year Outcome," 58th Annual Scientific Convention of the Society of Biological Psychiatry, May 5-17, 2003, San Francisco, California, 1 page.
Zabara, Jacob. "Inhibition of Experimental Seizures in Canines by Repetitive Vagal Stimulation," Department of Physiology, Temple University School of Medicine, Epilepsia, vol. 33, No. 6, dated 1992, Philadelphia, PA, pp. 1005-1012.
Bachman, David S. et al. "Effects of Vagal Volleys and Serotonin on Units of Cingulate Cortex in Monkeys," Laboratory of Brain Evolution and Behavior, National Institute of Mental Health, accepted Nov. 18, 1976, Brain Research, Elsevier/North-Holland Biomedical Press, pp. 253-269.
Bohning, Daryl E. et al. "Investigative Radiology: Feasability of Vagus Nerve Stimulation-Synchronized Blood Oxygenation Level-Dependent Functional MRI," A Journal of Clinical and Laboratory Research, vol. 36, No. 8, dated Aug. 2001, Lippincott Williams & Wilkins, pp. 469-479.
Devous, Michael D. et al. "Effects of Vagus Nerve Stimulation on Regional Cerebral Blood Flow in Treatment-Resistant Depression,"

(56) References Cited

OTHER PUBLICATIONS

National Institute of Mental Health—42nd Annual NCDEU Meeting: Poster Session II, retrieved from <http://www.nimh.nih.gov/ncdeu/abstracts2002/ncdeu2019.cfm>, printed Nov. 18, 2004, 1 page.

Hallowitz, Robert A. et al. "Effects of Vagal Volleys on Units of Intralaminar and Juxtalaminar Thalamic Nuclei in Monkeys," Laboratory of Brain Evolution and Behavior, National Institute of Mental Health, accepted Nov. 18, 1976, Brain Research, Elsevier/North-Holland Biomedical Press, pp. 271-286.

Requirement for Restriction/Election for U.S. Appl. No. 11/261,853 received from the United States Patent and Trademark Office (USPTO), dated Dec. 29, 2008, 13 pages.

Non-Final Office Action for U.S. Appl. No. 11/261,853 received from the United States Patent and Trademark Office (USPTO), dated Jun. 18, 2009, 8 pages.

Final Office Action for U.S. Appl. No. 11/261,853 received from the United States Patent and Trademark Office (USPTO), dated Oct. 7, 2009, 6 pages.

Advisory Action for U.S. Appl. No. 11/261,853 received from the United States Patent and Trademark Office (USPTO), dated Dec. 17, 2009, 3 pages.

Non-Final Office Action for U.S. Appl. No. 11/261,853 received from the United States Patent and Trademark Office (USPTO), dated Jun. 9, 2010, 6 pages.

Final Office Action for U.S. Appl. No. 11/261,853 received from the United States Patent and Trademark Office (USPTO), dated Nov. 10, 2010, 10 pages.

Notice of Allowance and Fees Due for U.S. Appl. No. 11/261,853 received from the United States Patent and Trademark Office (USPTO), dated Feb. 3, 2011, 7 pages.

* cited by examiner

USING PHYSIOLOGICAL SENSOR DATA WITH AN IMPLANTABLE MEDICAL DEVICE

CLAIM OF PRIORITY

This application is a divisional patent application of, and claims priority from, U.S. patent application Ser. No. 11/261,853, filed on Oct. 28, 2005 and entitled "Using physiological sensor data with an implantable medical device," which is incorporated hereby by reference in its entirety for all purposes.

FIELD OF THE DISCLOSURE

This disclosure relates generally to implantable medical devices, and, more particularly, to methods, apparatus, and systems for using data from a physiological sensor to affect an operation performed by an implantable medical device.

BACKGROUND

There have been many improvements over the last several decades in medical treatments for disorders of the nervous system, such as epilepsy and other motor disorders, and abnormal neural discharge disorders. One of the more recently available treatments involves the application of an electrical signal to reduce various symptoms or effects caused by such neural disorders. For example, electrical signals have been successfully applied at strategic locations in the human body to provide various benefits, including reducing occurrences of seizures and/or improving or ameliorating other conditions. A particular example of such a treatment regimen involves applying an electrical signal to the vagus nerve of the human body to reduce or eliminate epileptic seizures, as described in U.S. Pat. Nos. 4,702,254, 4,867,164, and 5,025,807 to Dr. Jacob Zabara, which are hereby incorporated in their entirety herein by reference in this specification.

Electrical stimulation of the vagus nerve (hereinafter referred to as vagus nerve stimulation therapy) may be provided by implanting an electrical device underneath the skin of a patient and performing a detection and electrical stimulation process. This type of stimulation is generally referred to as "active," "feedback," or "triggered" stimulation. Alternatively, the system may operate without a detection system once the patient has been diagnosed with epilepsy, and may periodically apply a series of electrical pulses to the vagus (or other cranial) nerve intermittently throughout the day, or over another predetermined time interval. This type of stimulation is generally referred to as "passive," "non-feedback," or "prophylactic," stimulation. The stimulation may be applied by an implantable medical device that is implanted within the patient's body.

State-of-the-art implantable medical devices generally deliver stimulation signals to one or more regions of a patient's body in a predetermined periodic cycle. Based upon the diagnosed disorder of the patient, a physician may determine a regimen of therapeutic stimulation signals to treat the disorder. The devices then execute the predetermined stimulation regimen. This regimen may be interrupted by predetermined interruption options, such as an external communication from a physician prompting a change in the regimen, a signal from the patient, etc.

The delivery of stimulation may cause physiological variations within a patient's body. However, state-of-the-art implantable medical devices generally do not allow for affecting the predetermined stimulation regimens in response to the various physiological variations. Barring active initiation of operational changes prompted by an external source, such as a physician, state-of-the-art implantable devices generally continue a predetermined treatment regimen despite physiological variations. This may cause the implantable medical device to become less responsive to changes in a patient's body.

In an attempt to alleviate some of these problems, designers have provided for altering the regimen based on an external input or input from the patient, for example, through a magnetic signal sent to the implantable device. However, this solution may not be sufficiently reactive to adequately address physiological variations resulting from stimulation regimens. Further, these solutions may require an assessment by an external source, such as a physician or the patient. By the time an external source examines the physiological variations, the patient's body may have gone through further changes, rendering any reaction to the original physiological variation obsolete.

Even though delivery of stimulation may cause specific physiological variations in the body, state-of-the-art implantable devices generally behave independently of such variations, at least in the short term. Long term changes may be provided by re-examination by a physician, i.e., re-diagnosis of a disorder, and then making further adjustments to the stimulation treatment. This may result in significant delay between the physiological changes that may occur due to stimulation, and the time period when manual adjustments to the stimulation regimen is made after examination from a physician. Therefore, efficient and effective reaction to physiological changes may not take place utilizing state-of-the-art implantable devices.

The present disclosure is directed to overcoming, or at least reducing, the effects of one or more of the problems set forth above.

SUMMARY

In one aspect, the present disclosure includes a method for providing an electrical neurostimulation therapy to a neural structure of a patient's body using an implantable medical device (IMD). A first electrical signal is provided using the implantable medical device. The first electrical signal is applied to the neural structure. An implanted sensor is provided. A physiological parameter is sensed using the implanted sensor. The physiological parameter includes at least one of a neurotransmitter parameter, a neurotransmitter breakdown product parameter, a neuropeptide parameter, and a glucocorticoid (GC) parameter. The first electrical signal is modified based upon the sensed physiological parameter to generate a second electrical signal. The second electrical signal is applied to the neural structure.

In another aspect, the present disclosure includes a method for providing an electrical neurostimulation therapy to a neural structure of a patient's body using an IMD. A first electrical signal having a first signal parameter selected from the group consisting of a current magnitude, a pulse width, a pulse period, a frequency, an on-time and an off-time, is provided. The first electrical signal is applied to a target portion of a patient's body to treat a disorder using an electrode operatively coupled to the implantable medical device. A sensor is provided. A physiological parameter is sensed using the sensor. The physiological parameter includes at least one of a neurotransmitter parameter, a neurotransmitter breakdown product parameter, a metabolite, a nucleotide parameter, a neuromodulator parameter, a neuromodulator breakdown product parameter, a peptide parameter, an enzyme parameter, a ligand parameter, a norepinephrine parameter, a glucocorticoid (GC) parameter, an amino acid parameter, a hormone parameter, a parameter of a bloodborne substance, a medication parameter, and a drug level in a portion of a patient's body. The first signal parameter is modified based upon the sensed physiological parameter to generate a second electrical signal. The second electrical signal is applied to the target portion of a patient's body.

In one aspect, the present disclosure includes an implantable medical device system for providing an electrical neuro stimulation therapy to a neural structure of a patient's body using an IMD. The implantable medical device system includes an implantable medical device (IMD) for providing a first electrical signal to a portion of a neural structure to treat a disorder. The IMD includes an electrode operatively coupled to the IMD. The electrode carries the first electrical signal from the IMD to the neural structure. The system includes a sensor operatively coupled to the IMD. The sensor is adapted to sense a physiological parameter. The physiological parameter includes at least one of a neurotransmitter parameter, a neurotransmitter breakdown product parameter, a neuropeptide parameter, a norepinephrine parameter, and a glucocorticoid (GC) parameter. The IMD also includes a control adapted to change a parameter of the first signal. The parameter is selected from the group consisting of a pulse width, a frequency, a polarity, and an amplitude, based upon the physiological parameter to generate a second electrical signal and to apply the second electrical signal to the neural structure.

In one aspect, the present disclosure includes a sensor to provide physiological data to an IMD to perform an adaptive stimulation process. The sensor is adapted to acquire data indicative of a neurotransmitter parameter in a patient's body. The neurotransmitter parameter includes at least one of a neurotransmitter level, a neurotransmitter breakdown product level, a neuropeptide level, a ligand level, an amino acid level, and a change in a glucocorticoid (GC) level in the patient's body.

BRIEF DESCRIPTION OF THE DRAWINGS

The disclosure may be understood by reference to the following description taken in conjunction with the accompanying drawings, in which like reference numerals identify like elements, and in which.

Figure 1A:
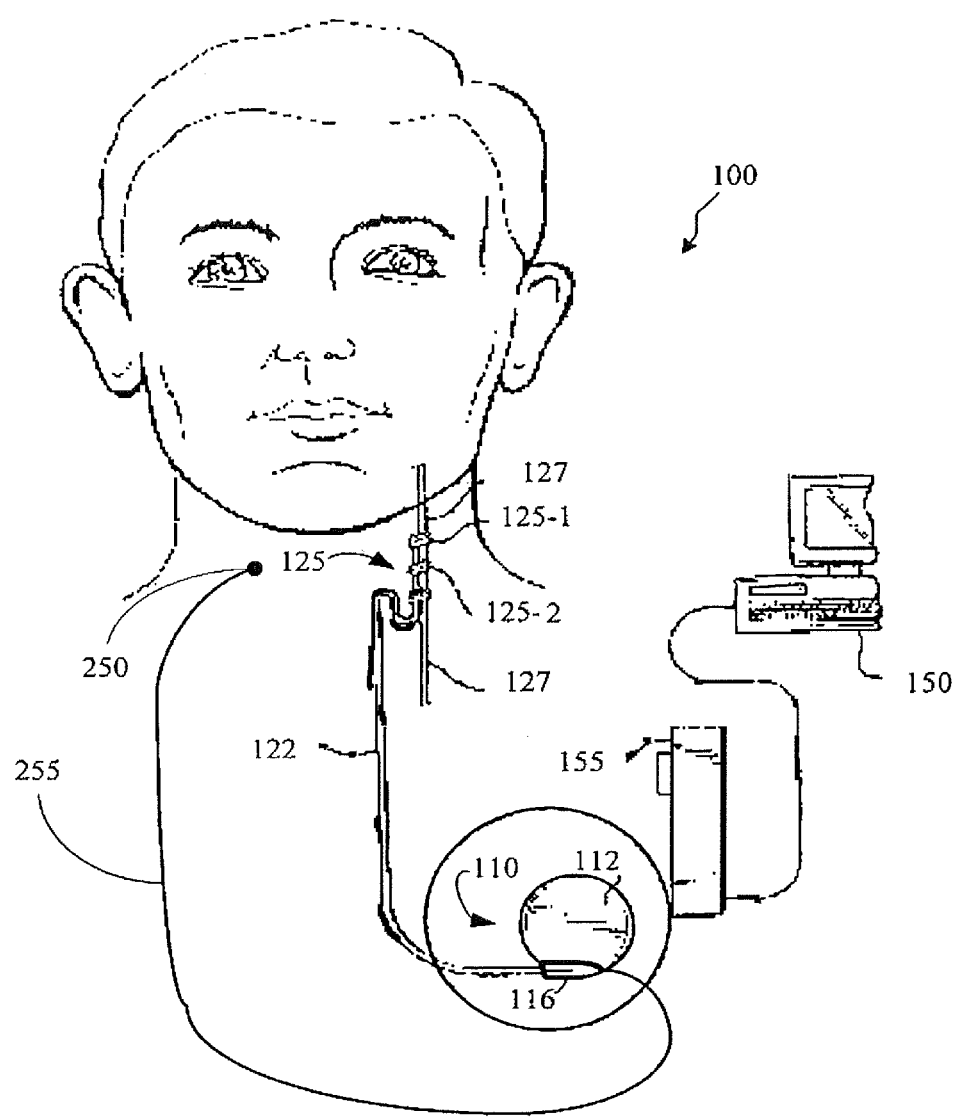
FIGS. 1A-1D provide stylized diagrams of an implantable medical device implanted into a patient's body for providing stimulation to a portion of the patient's body, in accordance with one illustrative embodiment.

While the disclosed embodiments are susceptible to various modifications and alternative forms, specific embodiments have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the scope of the disclosure as defined by the appended claims.

DETAILED DESCRIPTION

Illustrative embodiments are described herein. In the interest of clarity, not all features of an actual implementation are described in this specification. In the development of any such actual implementation, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

Embodiments disclosed herein provide for an adaptive therapeutic stimulation using an implantable medical device. Embodiments disclosed herein provide for using an implantable medical device for delivering a therapeutic stimulation based upon physiological data relating to a patient's body. The physiological data may be acquired by a sensor that is strategically implanted into the patient's body. The physiological data may include indications of a neurotransmitter level, a chemical level, an electrical level, a biological substance level, etc. Based upon the physiological data, at least one stimulation parameter may be adaptively modified for subsequent stimulations.

Although not so limited, a system capable of implementing embodiments disclosed herein is described below. FIGS. 1A-1D depict a stylized implantable medical system 100 for implementing one or more embodiments. FIGS. 1A-1D illustrate an electrical signal generator 110 having main body 112 including a case or shell 121 (FIG. 1A) with a header 116 (FIG. 1C) for connecting to leads 122. The generator 110 is implanted in the patient's chest in a pocket or cavity formed by the implanting surgeon just below the skin (indicated by a dotted line 145 in FIG. 1B), similar to the implantation procedure for a pacemaker pulse generator.

Figure 1B:
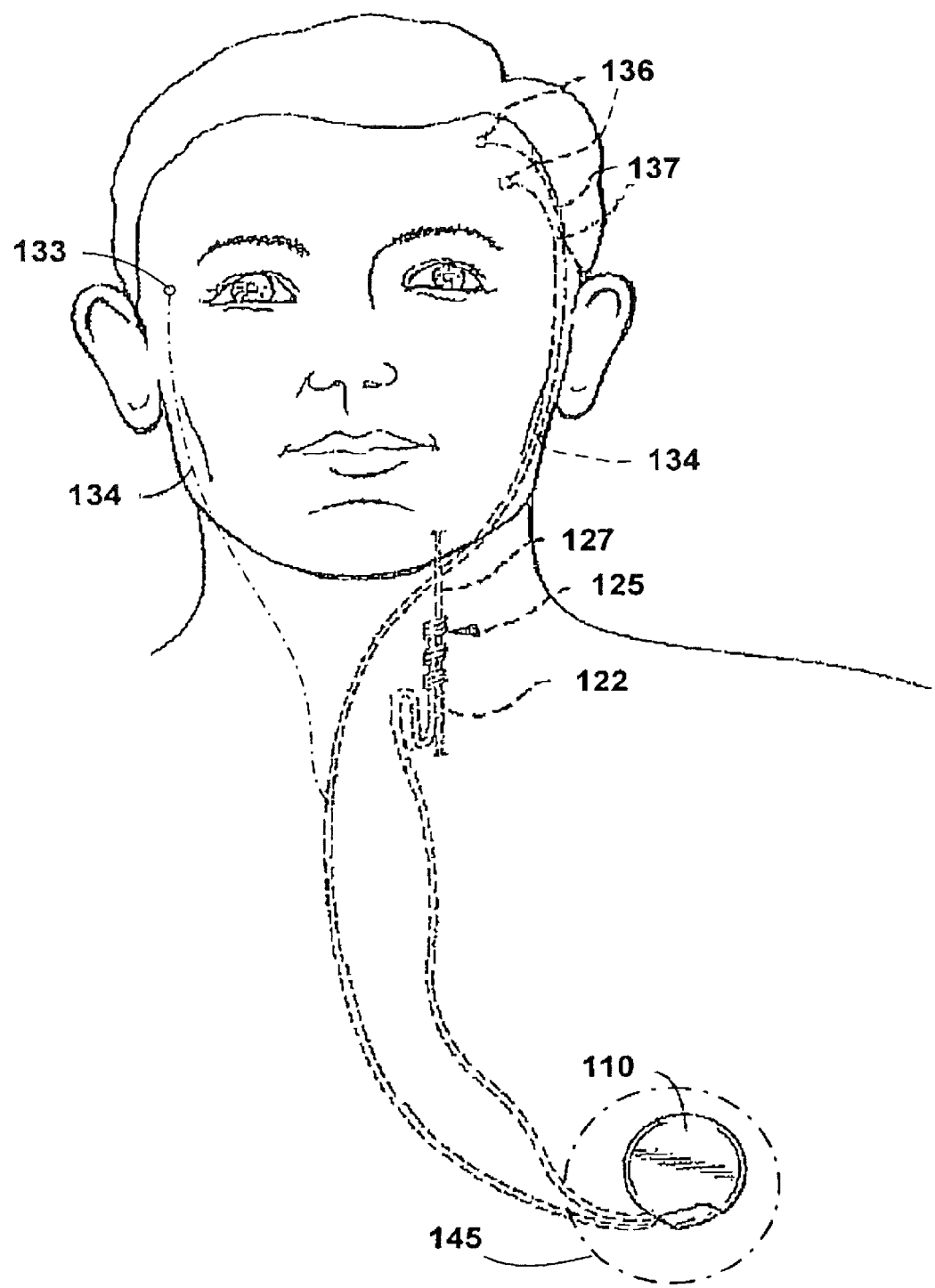
Figure 1C:
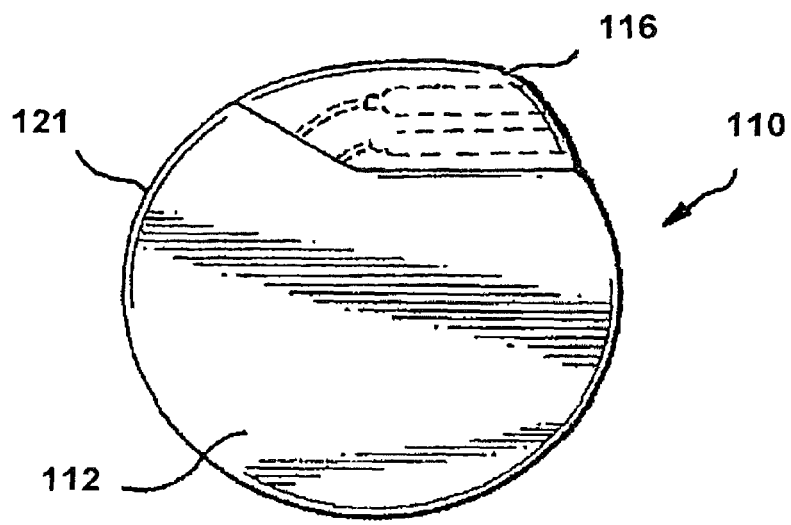
Figure 1D:
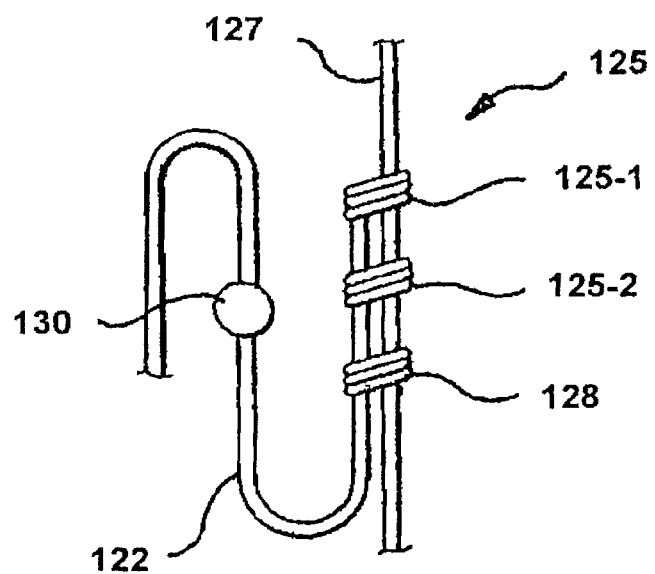

A stimulating nerve electrode assembly 125, preferably including an electrode pair, is conductively connected to the distal end of an insulated, electrically conductive lead assembly 122, which preferably includes a pair of lead wires (one wire for each electrode of an electrode pair). Lead assembly 122 is attached at its proximal end to connectors on the header 116 (FIG. 1C) on case 121. The electrode assembly 125 may be surgically coupled to a vagus nerve 127 in the patient's neck or at another location, e.g., near the patient's diaphragm. Other cranial nerves may also be used to deliver the electrical neuro stimulation signal. The electrode assembly 125 preferably includes a bipolar stimulating electrode pair 125-1, 125-2 (FIG. 1D), such as the electrode pair described in U.S. Pat. No. 4,573,481 issued Mar. 4, 1986 to Bullara. Suitable electrode assemblies are available from Cyberonics, Inc., Houston, Tex., USA, such as the Model 302 electrode assembly. However, persons of skill in the art will appreciate that many electrode designs could be used. The two electrodes are preferably wrapped about the vagus nerve, and the electrode assembly 125 may be secured to the nerve 127 by a spiral anchoring tether or loop 128 (FIG. 1D), such as that disclosed in U.S. Pat. No. 4,979,511 issued Dec. 25, 1990 to Reese S. Terry, Jr. and assigned to the same assignee as the instant application. Lead assembly 122 is secured, while retaining the ability to flex with movement of the chest and neck, by a suture connection 130 to nearby tissue (FIG. 1D).

In one embodiment, the open helical design of the electrode assembly 125 (described in detail in the above-cited Bullara patent), which is self-sizing and flexible, minimizes mechanical trauma to the nerve and allows body fluid interchange with the nerve. The electrode assembly 125 preferably conforms to the shape of the nerve, providing a low stimulation threshold by allowing a large stimulation contact area with the nerve. Structurally, the electrode assembly 125 includes two electrode ribbons (not shown), of a conductive material such as platinum, iridium, platinum-iridium alloys, and/or oxides of the foregoing. The electrode ribbons are individually bonded to an inside surface of an elastomeric body portion of the two spiral electrodes 125-1 and 125-2 (FIG. 1D), which may include two spiral loops of a three-loop helical assembly. The lead assembly 122 may include two distinct lead wires or a coaxial cable whose two conductive elements are respectively coupled to one of the conductive electrode ribbons. One suitable method of coupling the lead wires or cable to the electrodes 125-1, 125-2 includes a spacer assembly such as that disclosed in U.S. Pat. No. 5,531,778, although other known coupling techniques may be used.

The elastomeric body portion of each loop is preferably composed of silicone rubber, and the third loop 128 (which typically has no electrode) acts as the anchoring tether for the electrode assembly 125.

In certain embodiments, sensors such as eye movement sensing electrodes 133 (FIG. 1B) may be implanted at or near an outer periphery of each eye socket in a suitable location to sense muscle movement or actual eye movement. The electrodes 133 may be electrically connected to leads 134 implanted via a catheter or other suitable means (not shown) and extending along the jaw line through the neck and chest tissue to the header 116 of the electrical signal generator 110. When included in the system, the sensing electrodes 133 may be utilized for detecting rapid eye movement (REM) in a pattern indicative of a disorder to be treated, as described in greater detail below. The detected indication of the disorder can be used to trigger active stimulation.

Other sensor arrangements may alternatively or additionally be employed to trigger active stimulation. Referring again to FIG. 1B, electroencephalograph (EEG) sensing electrodes 136 may optionally be implanted and placed in spaced-apart relation on the skull, and connected to leads 137 implanted and extending along the scalp and temple, and then connected to the electrical signal generator 110 along the same path and in the same manner as described above for the eye movement electrode leads 134.

In alternative embodiments, temperature sensing elements and/or heart rate sensor elements may be employed to trigger active stimulation. In addition to active stimulation incorporating sensor elements, other embodiments utilize passive stimulation to deliver a continuous, periodic or intermittent electrical signal (each of which constitutes a form of continual application of the signal) to the vagus nerve according to a programmed on/off duty cycle without the use of sensors to trigger therapy delivery. Both passive and active stimulation may be combined or delivered by a single IMD. Either or both modes may be appropriate to treat the particular disorder diagnosed in the case of a specific patient under observation.

The electrical pulse generator 110 may be programmed with an external computer 150 using programming software of the type copyrighted by the assignee of the instant application with the Register of Copyrights, Library of Congress, or other suitable software based on the description herein, and a programming wand 155 to facilitate radio frequency (RF) communication between the computer 150 (FIG. 1A) and the electrical signal generator 110. The wand 155 and software permit non-invasive communication with the generator 110 after the latter is implanted. The wand 155 is preferably powered by internal batteries, and provided with a "power on" light to indicate sufficient power for communication. Another indicator light may be provided to show that data transmission is occurring between the wand and the generator.

A variety of stimulation therapies may be provided using the implantable medical system 100. Different types of nerve fibers (e.g., A, B, and C fibers being different fibers targeted for stimulation) respond differently to stimulation from electrical signals. More specifically, the different types of nerve fibers have different conduction velocities and stimulation thresholds and, therefore, differ in their responsiveness to stimulation. Certain pulses of an electrical stimulation signal, for example, may be below the stimulation threshold for a particular fiber and, therefore, may generate no action potential in the fiber. Thus, smaller or narrower pulses may be used to avoid stimulation of certain nerve fibers (such as C fibers) and target other nerve fibers (such as A and/or B fibers, which generally have lower stimulation thresholds and higher conduction velocities than C fibers). Additionally, techniques such as pre-polarization may be employed wherein particular nerve regions may be polarized before a more robust stimulation is delivered, which may better accommodate particular electrode materials. Furthermore, opposing polarity phases separated by a zero current phase may be used to excite particular axons or postpone nerve fatigue during long term stimulation.

As used herein, the terms "stimulating" and "stimulator" may generally refer to delivery of a signal, stimulus, or impulse to neural tissue for affecting neuronal activity of a neural tissue (e.g., a volume of neural tissue in the brain or a nerve). The effect of such stimulation on neuronal activity is termed "modulation"; however, for simplicity, the terms "stimulating" and "modulating", and variants thereof, are sometimes used interchangeably herein. The effect of delivery of the stimulation signal to the neural tissue may be excitatory or inhibitory and may potentiate acute and/or long-term changes in neuronal activity. For example, the effect of "stimulating" or "modulating" a neural tissue may include on one more of the following effects: (a) changes in neural tissue to initiate an action potential (bi-directional or uni-directional); (b) inhibition of conduction of action potentials (endogenous or externally stimulated) or blocking the conduction of action potentials (hyperpolarizing or collision blocking), (c) affecting changes in neurotransmitter/neuromodulator release or uptake, and (d) changes in neuro-plasticity or neurogenesis of brain tissue. Applying an electrical signal to an autonomic nerve may include generating a response that includes an afferent action potential, an efferent action potential, an afferent hyperpolarization, an efferent hyperpolarization, an afferent sub-threshold depolarization, and/or an efferent sub-threshold depolarization.

Particular embodiments provide for a method, apparatus, and a system for performing a sensor feedback analysis for providing an adaptive stimulation using an implantable medical device (IMD). A physiological data sensor, such as a neurotransmitter sensor, may be used to detect physiological variations and/or a physiological condition in a patient's body to affect the therapy stimulation provided by the IMD 200. Upon delivery of stimulation, various physiological changes (e.g., changes in chemical compounds, neurotransmitter level, a neurotransmitter breakdown product level, a metabolite level, a nucleotide level, a neuromodulator level, a neuromodulator breakdown product level, a peptide level, a ligand level, an amino acid level, a hormone level, a level of a bloodborne substance, a medication level, a drug level, electrical characteristics, etc., in the patient's body) may be detected and analyzed. This analysis may include comparing various sensed parameters, to corresponding predetermined reference parameters. Using this analysis, the treatment regimen for delivering therapy stimulation by the IMD 200 may be adjusted.

Further, in addition or alternative to modifying existing stimulation parameter(s), a second portion of the patient's body may be stimulated based upon the analysis described above. Adjusting the treatment regimen may include adjusting stimulation parameters to stimulate selective portions of a cranial nerve to activate a neuronal pathway consisting of the type: gustatory, olfactory, pro-inflammatory or anti-inflammatory, respiratory, cardiac, baroreceptor, somatosensory, and/or satiety. Cranial nerve stimulation may also be performed by particular embodiments in order to affect neurotransmitter pathways such as noradrenergic, serotoninergic, dopaminergic, catecholaminergic, GABAergic, opioidergic, and/or cholinergic pathways.

When delivering stimulation therapy, variations in the patient's body may occur. Data relating to these variations may be used to perform a characterization of a particular disorder (e.g., the severity, or lack thereof, of a disorder) to evaluate the effectiveness of the stimulation. Further, based upon the characterization of a disorder, such as depression, the therapy stimulation regimen may be increased or decreased accordingly. Physiological factors, such as serotonin levels, that may be directly or indirectly affected by the stimulation may be used to determine the effectiveness of the therapy stimulation. For example, serotonin re-uptake levels may be altered by the stimulation, affecting the depression state of a patient. Upon detecting the change in the serotonin uptake, therapy stimulation may be continued, increased, and/or decreased. In this manner, feedback associated with a disorder (e.g., depression) may be determined to provide an adaptive stimulation therapy.

The sensor provided by the embodiments disclosed herein may be capable of detecting a variety of physiological factors including chemical changes in a patient's body, biological changes (e.g., hormonal changes), electrical activity variations, neurotransmitter variations, etc., in a patient's body. Various algorithms may be provided in the IMD 200 to analyze the state of the physiological factors. Based upon this analysis, the stimulation treatment may be adaptively modified. Further, these physiological factors may be stored and/or reported to an external entity such as a physician, who may provide manual adjustments. Based upon the sensor feedback, in conjunction with the IMD, more effective and responsive treatment of a disorder may be performed.

Figure 2:
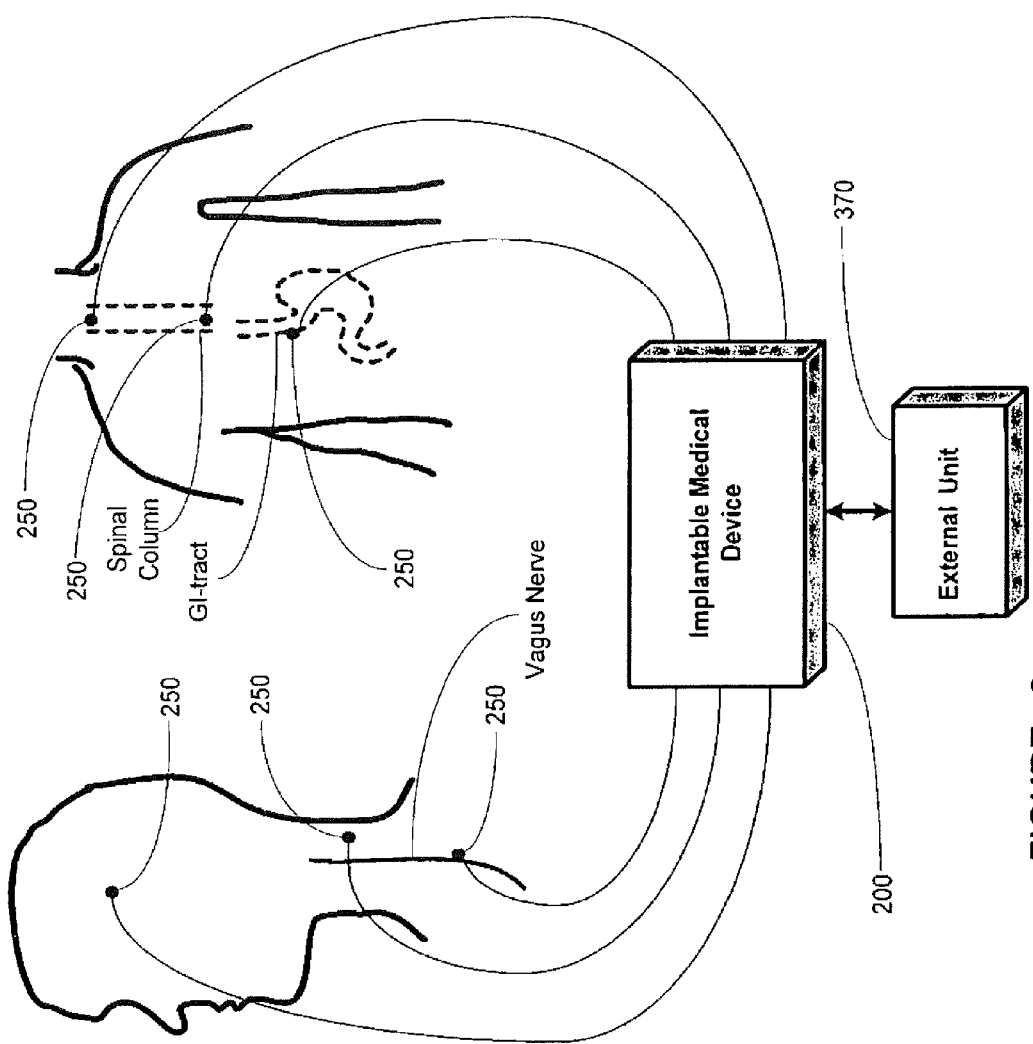
FIG. 2 illustrates a medical device system that includes an implantable medical device, one more sensors operatively coupled to the implantable medical device, and an external device, in accordance with one illustrative embodiment.

Turning now to FIG. 2, a stylized system description of an implantable medical device (IMD) 200 being coupled to one or more physiological sensors 250, in accordance with an illustrative embodiment, is provided. FIG. 2 illustrates exemplary locations in the patient's body upon which the sensor 250 may be implanted. For example, the sensor 250 may be implanted in the patient's brain, in the patient's neck, proximate a vagus nerve, the upper region of spinal column, the lower region of the spinal column, the gastrointestinal tract of the patient, etc. The sensor 250 may also be implanted into the bloodstream at various locations in the patient's body.

Data from the sensor 250 may be sent to the IMD 200. The IMD 200 may process the data and perfoilu various analyses relating to the physiological state of the patient. The IMD 200 may also perform various lookup functions and/or other types of calculations to assess the severity of a particular disorder. For example, an indication of serotonin levels in the patient's body may be used to determine a severity of depression in the patient. This information may be stored and/or sent to an external unit 370. Further details of the IMD 200, the sensor 250, and the external unit 370 are provided in various figures and the accompanying description below.

The system described in FIG. 2 may provide for a feedback adjustment of the stimulation therapy delivered by the IMD 200. The IMD 200 may also provide data relating to the physiological state of various portions of the patient's body to an external unit 370. This data received by the external unit 370 may be monitored and analyzed by a physician. Input from the external unit 370 and/or various sensors 250 positioned in the patient's body may be received by the IMD 200. Further, the IMD 200 may perform analyses using the acquired sensor data and provide therapy stimulation adjustments. This feedback may be performed continuously, periodically, or upon manual input from the external unit 370. Utilizing the feedback system described herein, various disorders such as depression, epilepsy, bulimia, diabetes, heart rhythm disorders, etc., may be treated.

Figure 3:
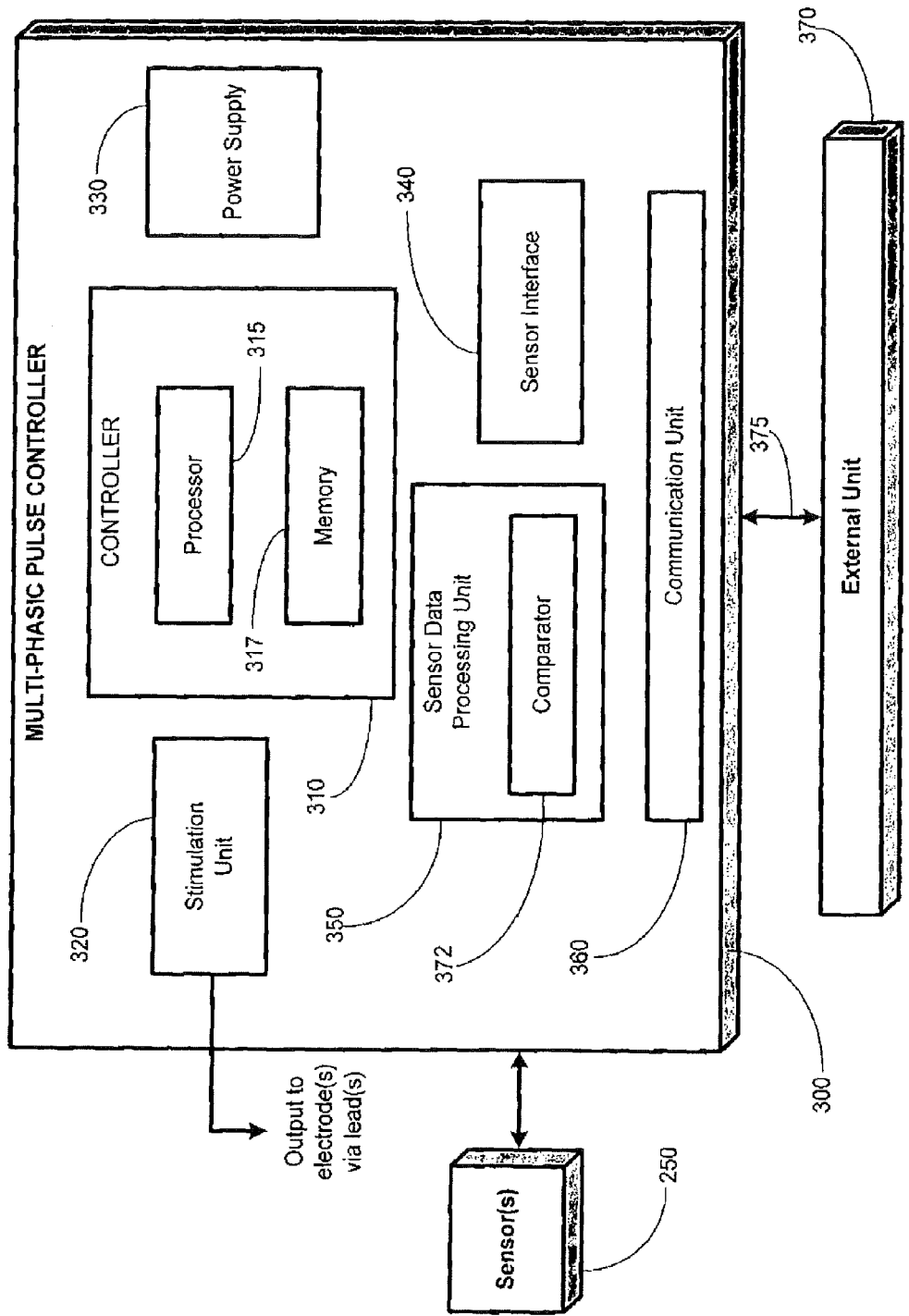
FIG. 3 illustrates a block diagram depiction of the implantable medical device of FIGS. 1A-1D, in accordance with one illustrative embodiment.

Turning now to FIG. 3 a more detailed block diagram depiction of the IMD 200 of FIG. 2 in accordance with one illustrative embodiment is provided. The IMD 200 may be used for stimulation to treat various disorders, such as epilepsy, depression, bulimia, heart rhythm disorders, etc. The IMD 200 may be coupled to various leads, e.g., 122, 134, 137 (FIGS. 1A, 1B, 1D). Stimulation signals used for therapy may be transmitted from the IMD 200 to target areas of the patient's body, specifically to various electrodes associated with the leads 122. Stimulation signals from the IMD 200 may be transmitted via the leads 122 to stimulation electrodes associated with the electrode assembly 125 (FIG. 1A). Further, signals from sensor electrodes, e.g., 133, 136 (FIG. 1B) associated with corresponding leads, e.g., 134, 137, may also traverse the leads back to the IMD 200.

The IMD 200 may include a controller 310 capable of controlling various aspects of the operation of the IMD 200. The controller 310 is capable of receiving internal data and/or external data and generating and delivering a stimulation signal to target tissues of the patient's body. For example, the controller 310 may receive manual instructions from an operator externally, or may perform stimulation based on internal calculations and programming. The controller 310 is capable of affecting substantially all functions of the IMD 200.

The controller 310 may include various components, such as a processor 315, a memory 317, etc. The processor 315 may include one or more micro controllers, micro processors, etc., that are capable of executing a variety of software components. The memory 317 may include various memory portions, where a number of types of data (e.g., internal data, external data instructions, software codes, status data, diagnostic data, etc.) may be stored. The memory 317 may include random access memory (RAM) dynamic random access memory (DRAM), electrically erasable programmable read-only memory (EEPROM), flash memory, etc.

The IMD 200 may also include a stimulation unit 320. The stimulation unit 320 is capable of generating and delivering a variety of electrical neurostimulation signals to one or more electrodes via leads. The stimulation unit 320 is capable of generating a therapy portion, a ramping-up portion, and a ramping-down portion of the stimulation signal. A number of leads 122, 134, 137 may be coupled to the MD 200. Therapy may be delivered to the leads 122 by the stimulation unit 320 based upon instructions from the controller 310. The stimulation unit 320 may include various types of circuitry, such as stimulation signal generators, impedance control circuitry to control the impedance "seen" by the leads, and other circuitry that receives instructions relating to the type of stimulation to be performed. The stimulation unit 320 is capable of delivering a controlled current stimulation signal to the leads and to the electrodes the leads 122.

The IMD 200 may also include a power supply 330. The power supply 330 may include a battery, voltage regulators, capacitors, etc., to provide power for the operation of the IMD 200, including delivering the stimulation signal. The power supply 330 includes a power-source battery that in some embodiments may be rechargeable. In other embodiments, a non-rechargeable battery may be used. The power supply 330 provides power for the operation of the IMD 200, including electronic operations and the stimulation function. The power supply 330 may include a lithium/thionyl chloride cell or a lithium/carbon monofluoride cell. Other battery types known in the art of implantable medical devices may also be used.

The IMD 200 also includes a communication unit 360 capable of facilitating communications between the IMD 200 and various devices. In particular, the communication unit 360 is capable of providing transmission and reception of electronic signals to and from an external unit 370. The external unit 370 may be a device that is capable of programming various modules and stimulation parameters of the IMD 200. In one embodiment, the external unit 370 includes a computer system that is capable of executing a data-acquisition program. The external unit 370 may be controlled by a healthcare provider, such as a physician, at a base station in, for example, a doctor's office. The external unit 370 may be a computer, preferably a handheld computer or PDA, but may alternatively include any other device that is capable of electronic communications and programming. The external unit 370 may download various parameters and program software into the IMD 200 for programming the operation of the implantable device. The external unit 370 may also receive and upload various status conditions and other data from the IMD 200. The communication unit 360 may be hardware, software, firmware, and/or any combination thereof. Communications between the external unit 370 and the communication unit 360 may occur via a wireless or other type of communication, illustrated generally by line 375 in FIG. 3.

The IMD 200 may receive various inputs from the sensor 250. In one embodiment the sensor 250 provides electrical signals indicative of a chemical response, an electrical response, a biological response, a neurotransmitter level, a neurotransmitter breakdown product level, a metabolite, a nucleotide level, a neuromodulator level, a neuromodulator breakdown product level, a peptide level, a ligand level, an amino acid level, a hormone level, a level of a bloodborne substance, a medication level, or a drug level indication associated with a portion of the patient's body, to the IMD 200. The sensor 250 illustrated in FIG. 3 may represent the aggregation of a plurality of sensors implanted in a variety of locations in a patient's body. The IMD 200 may also include a sensor interface 340. The sensor interface 340 is capable of receiving and organizing data from the sensor 250. The sensor interface 340 may include various interface circuitry to receive, perform buffering, and/or register the data received from the sensor 250. In one embodiment, the sensor 250 may provide digital data that has been converted within the sensor 250 to the IMD 200. In an alternative embodiment, the sensor 250 may provide analog-type data to the IMD 200. In one embodiment, the sensor interface 340 may also provide an analog-to-digital converter (A/D converter). The sensor interface 340 is capable of collecting sensor data and providing the sensor data to various modules within the IMD 200, such as the controller 310 and/or other units described herein.

The IMD 200 may also include a sensor data processing unit 350. The sensor data processing unit 350 is capable of correlating various physiological data to particular stimulation provided by the IMD 200. Further, the sensor data processing unit 350 may filter and/or perform digital signal processing upon the data from the sensor 250. The sensor data processing unit 350 may correlate, stack, and organize the sensor data. For example, the sensor data processing unit 350 may collect, organize, and correlate various sets of data relating to neurotransmitter level, a neurotransmitter breakdown product level, a metabolite, a nucleotide level, a neuromodulator level, a neuromodulator breakdown product level, a peptide level, a ligand level, an amino acid level, a hormone level, a level of a bloodborne substance, a medication level, or a drug level. The correlation of this data may include associating the sensor data to particular firings of stimulation signals.

The sensor data processing unit 350 may also include a comparator 372. The comparator 372 may include various comparator circuitry that are capable of comparing sensor data to previously acquired/stored sensor data and/or benchmark sensor data/tables that may be stored in the IMD 200. The sensor data processing unit 350 may provide compared, stacked, organized, correlated data to the controller 310, which may then perform further algorithm analysis upon the data. Additionally, data from the sensor data processing unit 350 may be sent to the external unit 370 via the communication unit 360. The physician examining the data via the external unit 370 may perform further analysis and diagnosis of a particular disorder and make further treatment adjustments. For example, based upon the newly acquired and correlated neurotransmitter levels, a physician and/or an algorithm within the IMD 200, may make a determination that serotonin re-uptake indicates that the depression level in a patient has changed and further adjustments to the treatment provided by the IMD 200 that should be performed. Other disorders may be diagnosed, analyzed, and/or characterized based upon the sensor data and in response adjustments to the IMD 200 may have been performed.

The IMD 200 is capable of delivering stimulation that can be intermittent, periodic, random, sequential, coded, and/or patterned. The stimulation signals may have an electrical stimulation frequency of approximately 0.1 to 2500 Hz. The stimulation signals may have a pulse width of in the range of approximately 1-2000 micro-seconds. The stimulation signals may have current amplitude in the range of approximately 0.1 mA to 10 mA. Stimulation may be delivered through either the cathode (−) electrode or anode (+) electrode. In one embodiment, the various blocks illustrated in FIG. 3 may include software unit, a firmware unit, a hardware unit, and/or any combination thereof.

Figure 4:
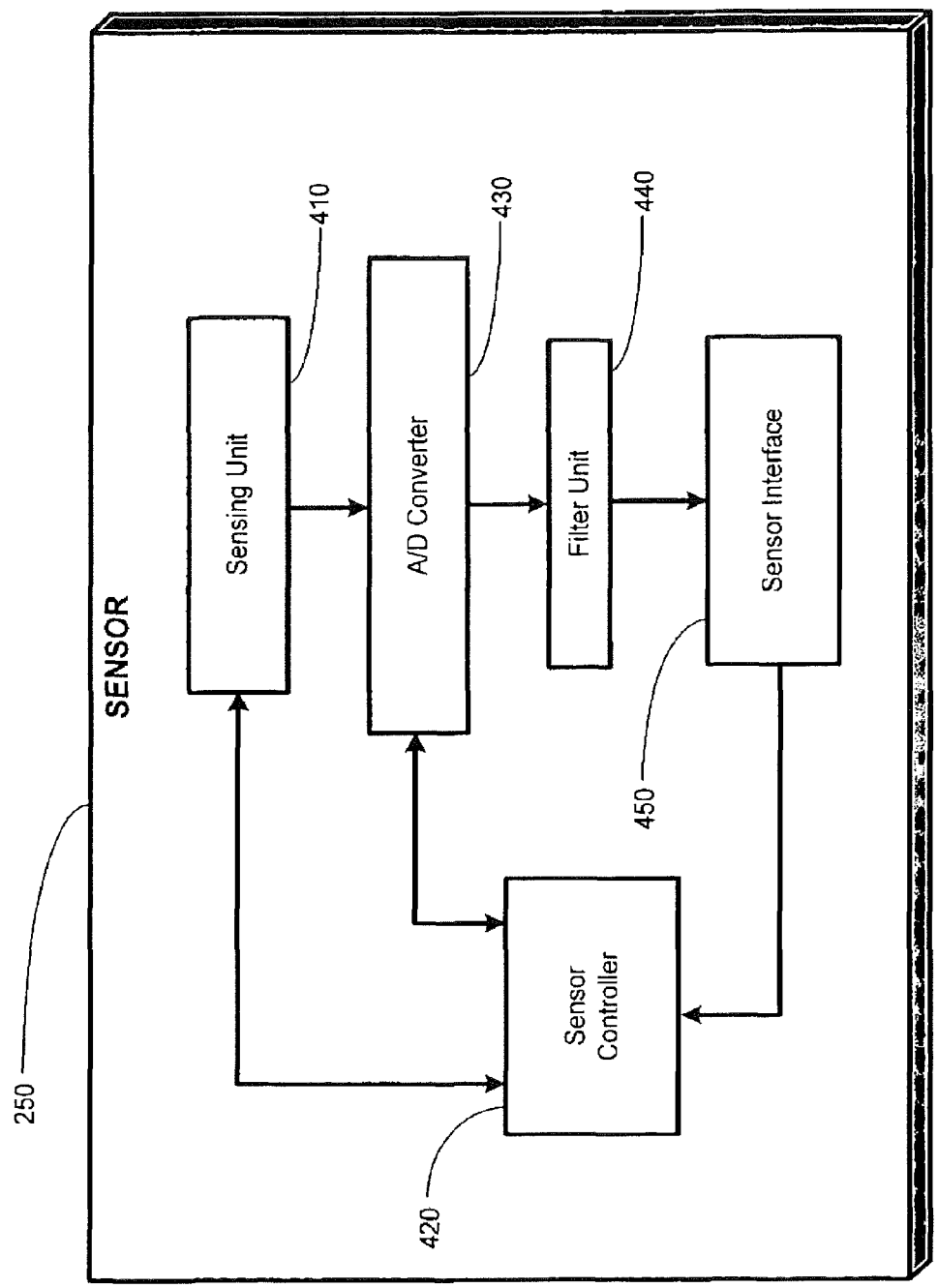
FIG. 4 illustrates a more detailed block diagram depiction of a sensor of FIGS. 2 and 3, in accordance with one illustrative embodiment.

Turning now to FIG. 4, a more detailed block diagram depiction of the sensor 250 in accordance with an illustrative embodiment is provided. The sensor 250 may include a sensor controller 420 that is capable of controlling the various functions performed by the sensor 250. The sensor controller 420 may be a microcontroller, a processor, etc. that may include integrated memory and program storage space. The sensor controller 420 is capable of receiving commands from the IMD 200 and/or from the external unit 370 and controlling the functions of the sensor 250 accordingly.

The sensor may include a sensing unit 410, which is capable of sensing one or more physiological responses or characteristics of a portion of a patient's body. A more detailed description of the sensing unit 410 is provided in FIG. 5 and accompanying descriptions below. Continuing to refer to FIG. 4, the sensor 250 may also include an A/D converter 430. The A/D converter 430 may receive analog signals from the sensing unit 410. The A/D converter 430 converts the analog data signals from the sensing unit 410 to generate equivalent digital data.

The sensor 250 may also include a filter unit 440 that is capable of filtering the sensed physiological data. In one embodiment, the filter unit 440 may be operatively positioned proceeding the A/D converter 430, wherein the filter unit 440 filters digital data. In an alternative embodiment, the filter unit 440 may be operatively positioned preceding the A/D converter 430, wherein the filter unit 440 in this embodiment filters analog data. Various filtering techniques known to those skilled in the art having benefited of the present disclosure, may be implemented into the filter unit 440, including a band-pass filter, a high-pass filter, a low-pass filter, etc.

The sensor 250 may also include a sensor interface 450. The sensor interface 450 is capable of receiving and transmitting data between the sensor 250 and other devices (i.e., the IMD 200, external unit 370, etc.). The sensor interface 450 is capable of receiving commands/data from the IMD 200 and/or the external unit 370. Additionally, the sensor interface 450 may provide physiological sensing data to the IMD 200 and/or to the external unit 370.

The sensor interface 450 may include various registers, transmission circuits, etc., to route data between the sensor 250 and the IMD 200. The sensor interface 450 may be capable of receiving and processing analog data, digital data, wired data, and/or wireless data.

In one embodiment, the sensing unit 410 may include portions developed from materials relating to nanotechnology. The sensing unit 410 may be capable of utilizing an electrochemical measurement based on the oxidation or reduction of a neurotransmitter or other chemical species. The sensing unit 410 may include an electrode held at a particular potential characteristic for a specific, predetermined neurotransmitter (i.e., the redox potential, which is described in further details below) with respect to a reference electrode. In this way, the neurotransmitter molecules may be absorbed upon the electrode surface. This may lead to the exchange of one or more electrons between the electrode and the neurotransmitter molecules. These electrons constitute the redox current. The redox currents are directly proportional to the concentration of the species in a solution. Therefore, the measurements from the electrode surface may be used to determine the concentration of a neurotransmitter.

In one embodiment, the sensing unit 410 may include a carbon nanotube/nanofiber array for electrical stimulation and/or acquiring/recording physiological characteristics. In this way, a process of performing an electrochemical acquiring/recording of neurotransmitter levels is possible. The sensing unit 410 may include very large scale integration (VLSI) components. The sensing unit 410 may be adapted to sense, store, and communicate information to the IMD 200 to provide stimulation therapy to increase or decrease neurotransmitter levels, and/or other chemical level(s) in a closed feedback system.

Figure 5:
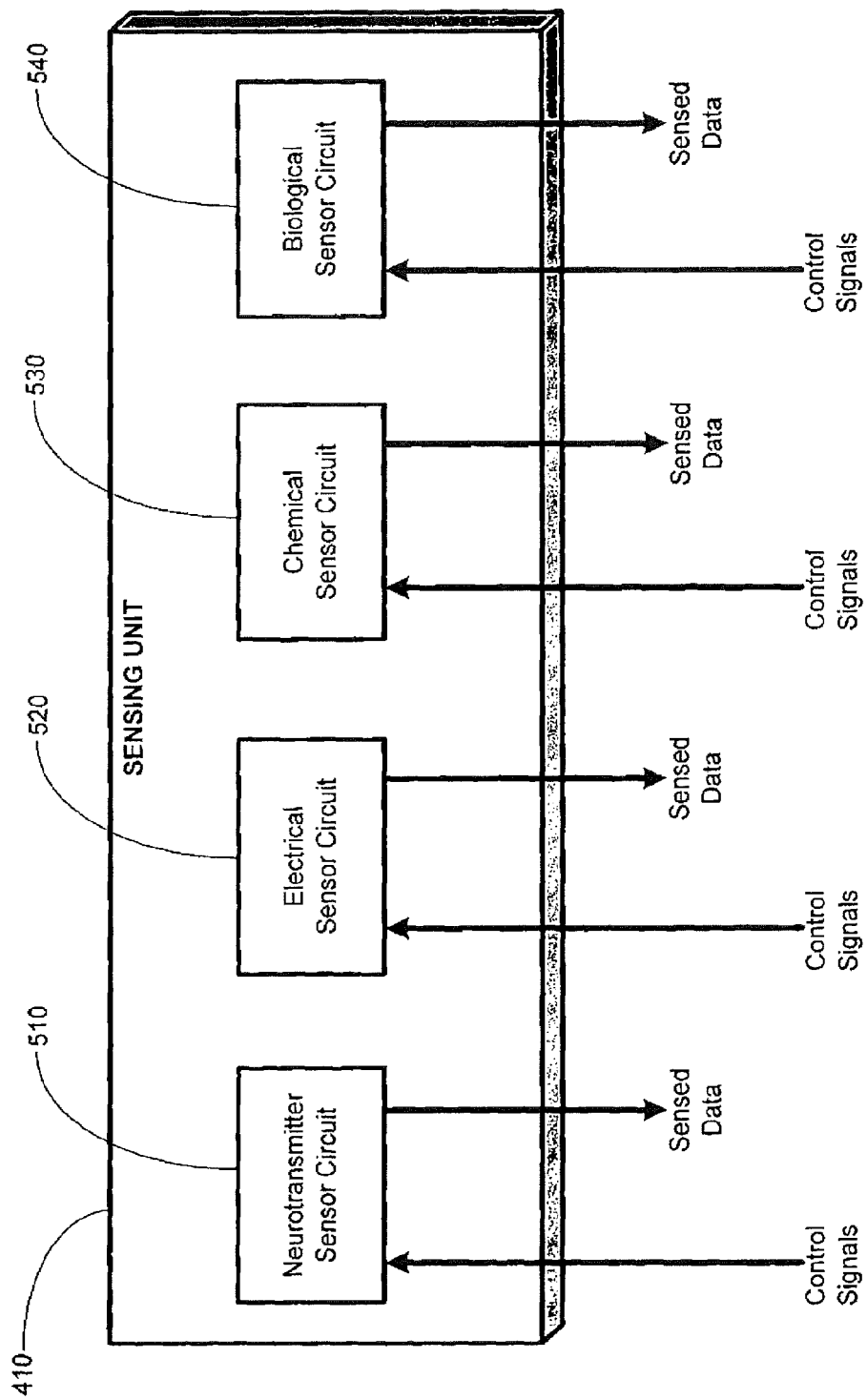
FIG. 5 illustrates a block diagram depiction of the sensing unit of FIG. 4, in accordance with one illustrative embodiment.

Turning now to FIG. 5, a block diagram depiction of the sensing unit 410 in accordance with an illustrative embodiment is depicted. The sensing unit 410 may include various types of sensing circuitry. The sensing unit 410 may include a neurotransmitter sensor circuit 510, an electrical sensor circuit 520, a chemical sensor circuit 530, and/or a biological sensor circuit 540. Each of the sensor circuits 510-540 may receive a control signal from sensor controller 420 to control its operations. Further, sensed data from each of the sensor circuits 510-540 is provided to other portions of the sensor 250.

The neurotransmitter sensor circuit 510 is capable of receiving and monitoring various neurotransmitter levels in a direct or in an indirect fashion. For example, the neurotransmitter, such as dopamine, may be detected via another indicator such as the Homovanillic Acid (HVA), which may be indicative of the level or concentration of dopamine. Dopamine may modulate the brain's reward mechanism and movement control. Other factors, such as 5-hydroxyindoleacetic acid (5HIAA) may be indicative of a level of the neurotransmitter serotonin. Neurotransmitters refer to chemicals that are used to delay, amplify, and/or modulate electrical signals between neurons. Neurotransmitters include small-molecule transmitters and neuroactive peptides. There are various small-molecule neurotransmitters that may be detected by the neurotransmitter sensor 510. For example, acetylcholine, 5 amines, 3 or 4 amino acids, purines, such as adenosine, ATP, GTP and/or their derivatives may be detected by the neurotransmitter sensor 510. Various neuroactive peptides may also be detected by the neurotransmitter sensor circuit 510. Neurotransmitters or the, breakdown products or metabolites of neurotransmitters may be detected by the IMD, and through subsequent analysis of the concentration levels, adjustments may be made to therapeutic stimulation.

In one embodiment, the neurotransmitter is dopamine, serotonin, acetylcholine, catecholamine, or nicotine.

Specific classes of neurotransmitters include, but are not limited to, peptides, enzymes, hormones, amino acids, and nucleotides, in addition to those described herein.

In one embodiment, the peptide is substance P, neuropeptide Y, neurokines, cytokines, interleukins, or lymphokines.

In one embodiment, the enzyme is adrenoceptor protein kinase, choline acetyltransferase, or acetylcholinesterase.

In one embodiment, the hormone is glucocorticoid (GC), serum cortisol, cortisol, prostaglandin, cholecystokinin (CCK), orexias, galinin, corticotrophin releasing hormone (CRH), or adrenocorticotropic hormone (ACTH).

In one embodiment, the amino acid is glutamate, gamma-aminobutyric acid (GABA), or glycine.

In one embodiment, the nucleotide is adenosine triphosphate (ATP) or guanosine triphosphate (GTP).

In neuronal transmission, some action potentials that travel to a neuron cell-body cause a resultant rapid depolarization which causes calcium ion channels to open. Calcium then may stimulate the transport of vesicles to synaptic membranes. The vesicles and cell membranes may fuse, leading to the release of packaged neurotransmitter. This action is called exocytosis. The neurotransmitters may then diffuse across the synaptic cleft to bind to receptors. The receptors may be ionotropic and metabolic receptors. A neurotransmitter's effect is influenced by its receptors.

Neurotransmitters may cause either excitatory or inhibitory post synaptic potentials. Neurotransmitters may help the initiation of a nerve impulse in a receiving neuron. Alternatively, neurotransmitters may discourage such an impulse by modifying the local membrane voltage potential. This modification of the voltage potential may be detected by the electrical sensor circuit 520.

Further, neurotransmitters are removed from the synaptic cleft by the process of re-uptake. Re-uptake provides for the prevention of continuous stimulation or inhibition of the firing of post synaptic neurons. In other words, re-uptake is necessary to control either the excitatory or inhibitory post synaptic potentials. The electrical sensor unit 520 may be capable of detecting voltage levels that are indicative of the excitatory or inhibitory states of post synaptic potentials. This information may lead to a determination of the state of a particular disorder, such as depression. The neurotransmitter sensor circuit 510 is capable of detecting neurotransmitters such as dopamine and/or serotonin Serotonin is generally released by cells in the brainstem region (i.e., raphe nuclei). A sensor 250 may be positioned proximate to the brainstem region such that detection of the neurotransmitter, serotonin, is facilitated. In one embodiment, the sensor may consist of an implantable microdialysis probe coupled to a neurochemical analyzer.

Serotonin re-uptake inhibition may be provided by the stimulation delivered by the IMD 200. This may potentiate serotonin's effect, thereby changing the depression level in the patient's body. This process may be detected, monitored, and controlled by using data from the neurotransmitter sensor circuit 510 and/or the electrical sensor 520 to monitor the effects of the treatment provided by the IMD 200. Serotonin may affect the biochemistry of depression, migraine, bi-polar disorder, and/or anxiety. Further, serotonin may affect sexuality and appetite disorders in a patient's body. The level of serotonin may be affected by the stimulation delivered by the IMD 200, wherein the stimulation may be based upon data from the neurotransmitter sensor circuit 510.

The neurotransmitter sensor circuit 510 may also detect dopamine levels in the patient's body. Dopamine generally activates dopamine receptors and is also a neurohormone released by the hypothalamus. This hormone may also be detected by the biological sensor unit 540, which is capable of detecting biological substance in the patient's body. Dopamine may act upon the sympathetic nervous system, the result of which may include increasing heart rate, increasing blood pressure, increasing respiration rate, etc. Other disorders, such as Parkinson's disease, may be affected by the IMD 200 by varying dopamine levels, which may be detected and controlled in a feedback control manner using data from the neurotransmitter sensor circuit 510 and/or data from the biological sensor unit 540. Additionally, chemical indications such as HVA, 5-hydroxyindoleacetic acid (5HIAA) acid, etc., may provide an indication of the respective levels of dopamine and serotonin in the body. This chemical detection may be provided by the chemical sensor unit 530.

Various disorders may affect the neurotransmitter passageways inside the patient's body, which may be detected by the sensing unit 410. Other components, such as nitric oxide, may also be detected by the sensing unit 410, which may affect immune system responses. Therefore, data from the sensor may be used by the IMD 200 to treat immune-related disorders.

The electrical sensor circuit 520 is capable of detecting electrical factors such as a redox reaction. Redox reaction generally refers to oxidation and reduction associated with transfer of one or more electrons from a donor to an acceptor of chemical species. The oxidation-reduction reaction may accompany a change in energy called free energy. The free energy may cause a flow of electrons that generates a redox potential, which may be measured by the electrical sensor circuit 520. Other factors like metabolite, etc., may also be detected by the various circuitry of the sensing unit 410.

The neurotransmitter sensor circuit 510 may detect the various neurotransmitter-related physiological conditions such as a neurotransmitter level, a neurotransmitter breakdown product level, a metabolite, change in a neurotransmitter breakdown product level, a peptide level, a change in peptide level, a ligand level, a change in a ligand level, an amino acid level, a change in an amino acid level, a medication level, change in a medication level, a drug level, change in a drug level, change in hormone, change in a hormone level, change in a glucocorticoid (GC), change in a glucocorticoid (GC) level, and/or a change in level of a bloodborne substance.

The chemical sensor unit 530 is capable of sensing various chemical factors in the patient's body, such as a change in the level of serum cortisol, cortisol level, neuropeptide Y, acetylcholine, dopamine, serotonin, prostaglandins, glucocorticoids, catecholamines, adrenoceptor g-protein kinase, glutamate, nicotinic, neuropeptide Y, GABA (A and B), neurokine-a, neurokine-3, choline aceytransferanse, acetylcholinesterase, cytokines, cholecystokinin (CCK), aglutamate, orexins, and/or galinin. Various other chemical physiological factors in the patient's body may also be detected by the sensing unit 410.

The biological sensor unit 540 is capable of sensing various biological factors in the patient's body, such as various hormone levels, acetylcholine corticotrophin releasing hormone (CRH), and/or adrenocorticotropic hormone (ACTH). These physiological factors may be analyzed to determine the response as to various physiological states of a patient's body resulting from a stimulation.

Figure 6:
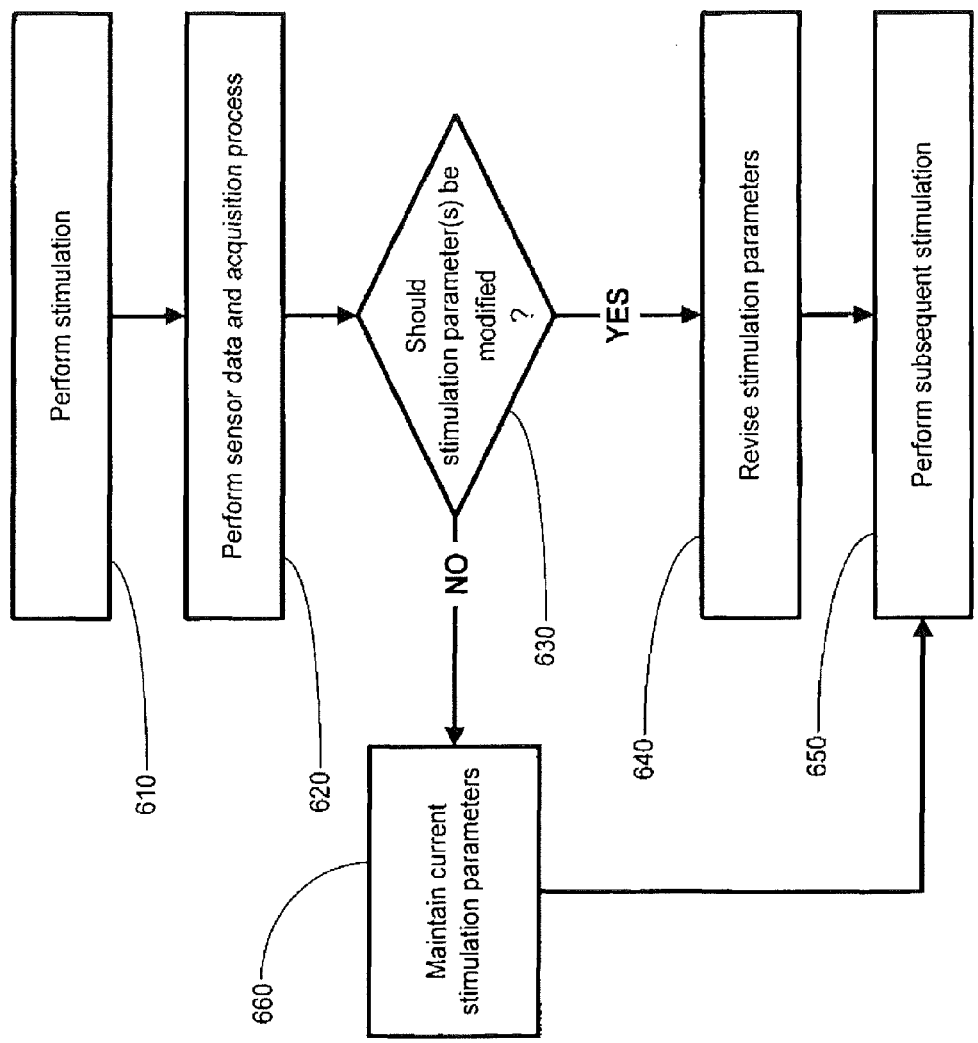
FIG. 6 illustrates a flowchart depiction of a method of performing an adaptive stimulation process using sensor feedback, in accordance with a first illustrative embodiment.

Turning now to FIG. 6, a flowchart depiction of a method for performing an adaptive stimulation control process using sensor data in accordance with one illustrative embodiment is depicted. In one embodiment, the IMD 200 performs a delivery of stimulation therapy based upon a predetermined set of parameters (block 610). Subsequent to the delivery of stimulation, the IMD 200 may perform a sensor data acquisition and analysis process (block 620). This process may include acquiring one or more types of physiological data from the sensor 250 and performing an analysis to determine a physiological condition of the patient. For example, the effect of stimulation provided upon a particular disorder such as depression may be analyzed during this process. A more detailed description of the sensor data acquisition and analysis process of block 620, are provided in FIG. 7 and the accompanying description below.

Continuing referring to FIG. 6, upon performing the acquisition of sensor data and analyzing the data, the IMD 200 may determine whether stimulation parameters should be modified (block 630). A decision to modify stimulation parameters may be based upon the characteristic(s) relating to various physiological conditions, such as a detected increase in the re-uptake of serotonin levels when treating depression. Based upon this analysis, the IMD 200 may, for example, determine that a reduced amount of stimulation may now be needed since serotonin re-uptake has increased, thereby reducing the possibility of an onset of a severe depression episode. Other factors such as neurotransmitter levels, electrical indications in the patient's body, chemical indications and/or biological indications may be detected and analyzed to determine whether an increase, a decrease, or no change to the stimulation parameters is desirable. Other modifications may include performing a stimulation in a second portion of the patient in response to a physiological factor.

Upon detecting that the stimulation is to be modified, revised stimulation parameter(s) may be implemented by the IMD 200 (block 640). Various algorithms and tables may be stored in the IMD 200 to allow for a comparison and analysis of the acquired sensory data with reference data in order to adjust stimulation parameters. Alternatively, sensor signal and analysis may be communicated to an external unit 370. In this case, a physician may perform an analysis and manually instruct the IMD 200 to modify its stimulation parameters. Upon modification of the stimulation parameters, the IMD 200 may perform a subsequent stimulation based on the modified parameters (block 650). This process may then follow another sensor analysis and the entire process indicated in FIG. 6 may be repeated.

In one embodiment, the sensing of the data sensor data may be performed periodically based upon a predetermined interval. In an alternative embodiment, sensing of the data sensor data may be performed reactively based upon an event detected by the IMD 200. In yet another embodiment, the sensing of the data sensor data may be performed by external prompt (e.g., a prompt from a physician or the patient) from the external unit 370. Further, the sensing of the data sensor data may be performed based on any combination of the "predetermined interval" approach, the "reactive" approach, and the "external prompt" approach.

When the IMD 200 determines that based upon the data and the sensory analysis process that the stimulation should not be monitored or modified, the IMD 200 merely maintains the current stimulation patterns and performs a subsequent stimulation (block 660). In this manner, physiological conditions may be monitored and characterization of a disorder may be made to provide an adaptive adjustment of the stimulation provided by the IMD 200. Therefore, a feedback loop may be established using the sensor data and analysis by the IMD 200 and/or external input to provide an adaptive adjustment of the one or more stimulation parameters.

Figure 7:
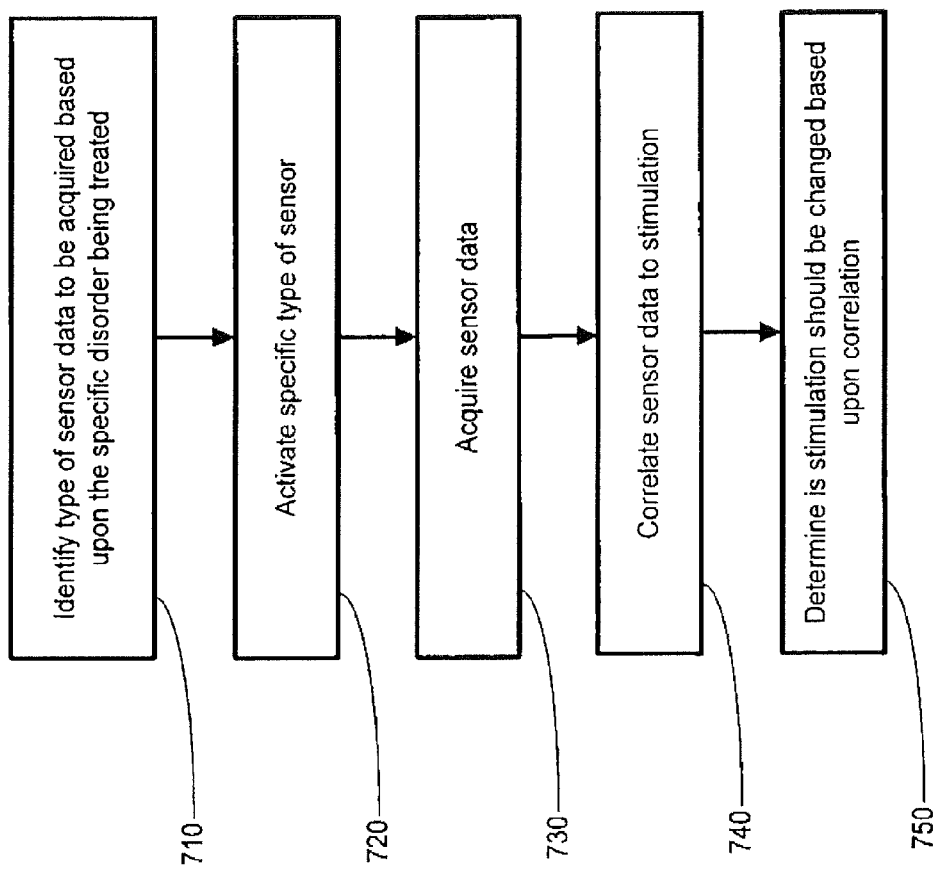
FIG. 7 illustrates a more detailed flowchart depiction of a method of performing the sensor data acquisition and analysis process of FIG. 6, in accordance with one illustrative embodiment.

Turning now to FIG. 7, a flowchart depiction of performing the sensor data acquisition and analysis process of block 620, is illustrated. The IMD 200 may identify the type of sensor data to be acquired based upon the specific disorder being treated by the IMD 200 (block 710). For example, in the case of treating depression, various neurotransmitters may be analyzed. Accordingly, the neurotransmitter sensor circuit 510 in the sensing unit 410 may be activated (see FIGS. 4 and 5). Continuing referring to FIG. 7, if the IMD 200 has been programmed to analyze indication(s) of the neurotransmitter rather than the neurotransmitter itself, the electrical sensor circuit 520, chemical sensor circuit 530, and/or biological sensor circuit 540 may be activated by the IMD 200 (block 720).

Upon activation of the desired type of sensor data to be acquired, one or more specific sensor circuits 510-540 in the sensor 250 are activated.

Based upon the activation of one or more sensor circuits 510-540, the corresponding sensor data may be acquired (block 730). The timing of the acquisition may be determined based on predetermined rules, such as a predetermined protocol for following a stimulation period with an acquisition of physiological data. Therefore, indications of physiological variations in the patient's body, such as data relating to changes in the neurotransmitter levels, may be acquired and correlated to the preceding stimulation regimen (block 740). Based upon this correlation, the IMD 200 may determine whether the stimulation parameters should be changed (block 750). In other words, if it is determined that based upon the correlation, the desired affect has been achieved, a parameter relating to the stimulation (e.g., amplitude) may be reduced. Alternatively, if significant physiological changes are detected, the intensity of the stimulation, duration, and/or other parameters associated with the stimulation may be modified to prompt a more appreciable physiological response to the stimulation.

Figure 8:
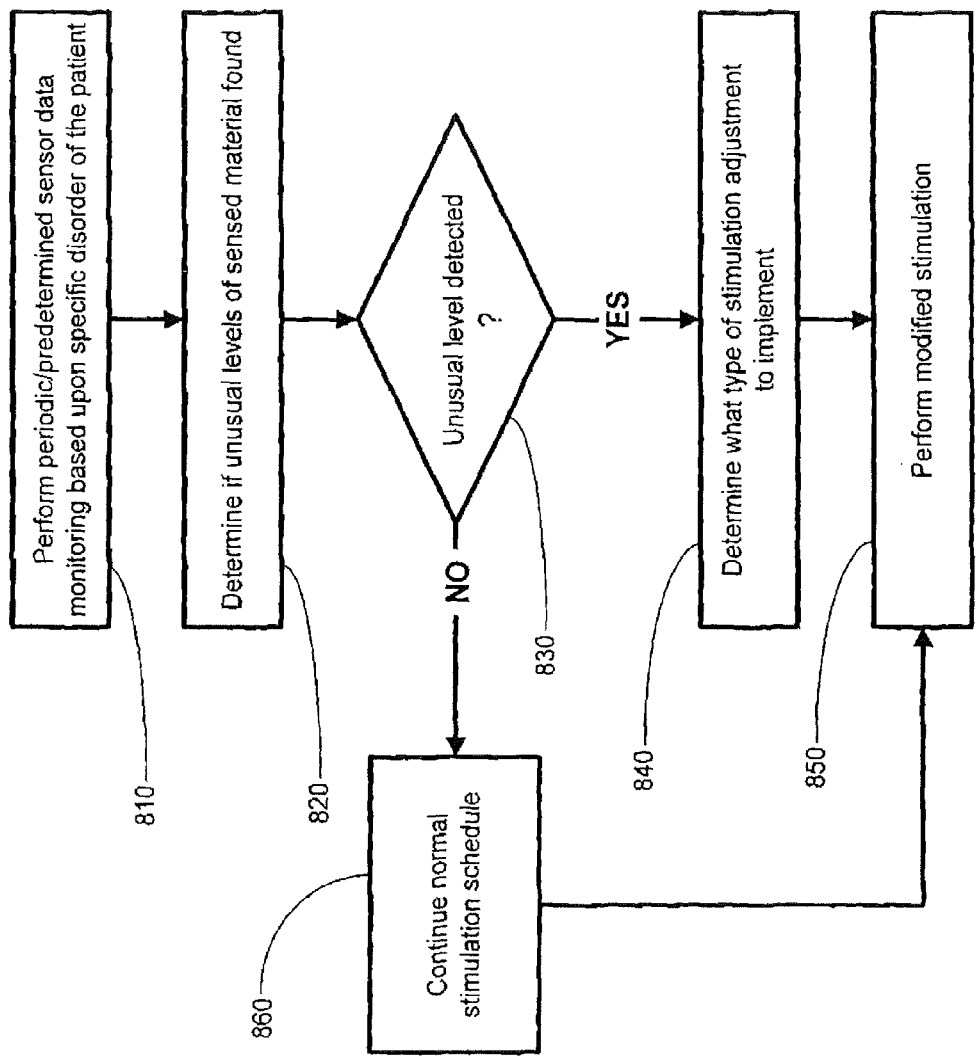
FIG. 8 illustrates a flowchart depiction of a method of performing the adaptive stimulation process using a sensor feedback process, in accordance with a second illustrative embodiment.

Turning now to FIG. 8, a flowchart depiction of performing the sensor feedback control of the IMD 200 in accordance with an alternative embodiment is provided. In this embodiment, regardless of whether a stimulation has been recently performed or not, the sensor 250 may be activated to perform a periodic or predetermined sensor data monitoring process (block 810). This may include monitoring specific electrical, chemical, biological, and/or neurotransmitter levels. The sensing process may be based upon the specific disorder being treated by the IMD 200. Based upon the sensing the data, the IMD 200 may process and analyze the data to determine whether unusual responses resulting from the stimulation has occurred (block 820). The comparator 372 may use baseline/reference comparison data to compare the current level of physiological characteristics detected by the sensor. This may provide an indication as to whether unusual levels of the sensed materials are found.

A determination is made whether unusual level(s) relating to the sensed characteristic(s) have been detected (block 830). For example, an unusual amount of serotonin may indicate that sufficient re-uptake has not taken place. If it is determined that no unusual level of physiological characteristic has been detected, the IMD 200 may continue a normal stimulation schedule as predetermined (block 850). This block may be looped back to the block 810 where a periodic sensor data acquisition is performed. If normal levels have been detected, the IMD 200 may simply continue performing predetermined, periodic stimulation and continue to periodically monitor the sensor data. Additionally, event-driven and/or manually provoked sensing may also be implemented.

If it is determined that the detected sensed characteristic level was unusual (block 830), the IMD 200 may determine the type of stimulation adjustment to implement (block 840). In other words, if unusual levels of sensed material have been detected, various analyses, comparisons, and algorithms may be performed to determine whether to increase, decrease, or otherwise change the stimulation parameters based on the various factors detected. Based upon a determination of the type of stimulation adjustment to be implemented, a resulting modified stimulation is delivered (block 850). For example, increased intensity of a stimulation signal may be now be provided in response to an indication that excessive neurotransmitters have been detected. Therefore, a stimulation may be provided to prompt additional re-uptake of a neurotransmitter (e.g., causing an increase in serotonin re-uptake to decrease the intensity of depression in a patient).

Utilizing the concepts provided herein, an adaptive stimulation process may be implemented by modifying stimulation parameters based upon detected sensor data. Various characteristics, such as chemical changes, hormonal changes, electrical activity changes, neurotransmitter level changes, etc., may be detected and analyzed. Based upon this analysis, feedback correction/adjustment of stimulation parameters may be performed by the IMD 200. In this manner, more efficient response to a patient's reaction to stimulation may be performed by the IMD 200. In this way targeted treatment may be adaptively performed, thereby improving treatment of various disorders using an implantable medical device.

The particular embodiments disclosed above are illustrative only and may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the disclosure. Accordingly, the protection sought herein is as set forth in the claims below.

What is claimed is:

1. An implantable medical system comprising:
 an implantable medical device (IMD) operative to provide a first electrical signal;
 an electrode coupleable to the IMD, the electrode operative to deliver the first electrical signal from the IMD to a neural structure to cause afferent nerve impulses or afferent and efferent nerve impulses to propagate along the neural structure away from the electrode;
 a sensor coupleable to the IMD, the sensor operative to sense a physiological parameter, wherein the physiological parameter includes at least one of a neurotransmitter breakdown product parameter, a neuropeptide parameter, or an amino acid parameter; and
 a controller operative to:
  change a signal parameter of the first electrical signal based upon the physiological parameter to generate a second electrical signal;
  apply the second electrical signal to the neural structure, wherein the signal parameter includes at least one of a pulse width, a frequency, a polarity, or an amplitude, and wherein the first and second electrical signals are applied to the neural structure to treat depression; and
  in response to the applied first and second electrical signals, determine a severity of the depression based on the sensed physiological parameter.

2. The implantable medical system of claim 1, wherein determining the severity of the depression is based on a lookup function performed by the IMD.

3. The implantable medical system of claim 1, wherein the sensor further comprises:
 a sensor controller operative to control timing of sensing of the physiological parameter relative to a stimulation period based on a predetermined protocol to enable correlating the stimulation period with the physiological parameter, and
 wherein the IMD further comprises:
  a stimulation unit coupled to the controller, the stimulation unit operative to provide the first and second electrical signals;
  a sensor interface operative to provide communications with the sensor;
  a sensor data processing unit operative to process sensor data from the sensor, the sensor data processing unit comprising a comparator operative to compare the sensor data with corresponding stored data to provide compared data, the sensor data processing unit also operative to correlate at least one of the sensor data and the compared data to the first electrical signal based on the predetermined protocol; and
  a communication unit operative to communicate with an external unit.

4. The implantable medical system of claim 1, wherein the sensor is configured to be implanted in at least one of a spinal column, a brain stem, a brain, a cranial nerve, a neural tissue, or a gastro-intestinal tract of a patient's body, and wherein the amino acid parameter comprises at least one of a glutamate parameter, and a glycine parameter.

5. The implantable medical system of claim 1, wherein the neural structure includes a spinal column and at least one of a vagus nerve, a brain stem, a trigeminal nerve, a hypoglossal nerve, or an accessory nerve.

6. The implantable medical system of claim 1, wherein the afferent nerve impulses are configured to effect neuronal activity of a brain of a patient resulting in changes in the physiological parameter.

7. An implantable medical device (IMD) comprising:
 a stimulation unit operative to provide a first electrical signal to a neural structure such that afferent nerve impulses propagate along the neural structure to a brain of a patient;
 a sensor interface operative to receive data from a sensor, the data corresponding to a sensed physiological parameter, the sensed physiological parameter including at least one of a neurotransmitter breakdown product parameter, a neuropeptide parameter, or an amino acid parameter;
 a sensor controller, the sensor controller operative to control timing of sensing of the sensed physiological parameter relative to a stimulation period based on a predetermined protocol to enable correlating the stimulation period with the sensed physiological parameter; and
 a controller operative to:
  change a signal parameter of the first electrical signal based on the data corresponding to the sensed physiological parameter to generate a second electrical signal;
  apply the second electrical signal to the neural structure, wherein the signal parameter includes at least one of a pulse width, a frequency, a polarity, or an amplitude, and wherein the first and second electrical signals are applied to the neural structure to treat depression; and
  in response to the applied first and second electrical signals, determine a severity of the depression based on the sensed physiological parameter.

8. The implantable medical device of claim 7, further comprising:
 a communication unit operative to communicate with an external unit.

9. The implantable medical device of claim 7, further comprising:
 a sensor data processing unit comprising a comparator operative to compare the data with corresponding stored data to provide compared data, the sensor data processing unit also operative to correlate at least one of the data and the compared data to the first electrical signal based on the predetermined protocol.

10. The implantable medical device of claim 7, wherein the afferent nerve impulses are configured to effect neuronal activity of the brain of the patient resulting in changes in the sensed physiological parameter.

11. An implantable medical system comprising:
 an implantable medical device (IMD) operative to provide a first electrical signal, the IMD comprising a communication unit that is configured to transmit first communication signals to an external unit and to receive second communication signals from the external unit;
 an electrode coupleable to the IMD, the electrode to deliver the first electrical signal to a neural structure to cause afferent nerve impulses or afferent and efferent nerve impulses to propagate along the neural structure away from the electrode;
 a sensor coupleable to the IMD, the sensor operative to sense a physiological parameter, wherein the physiological parameter includes at least one of a neurotransmitter breakdown product parameter, a neuropeptide parameter, or an amino acid parameter;

a sensor controller operative to control timing of sensing of the physiological parameter relative to a stimulation period based on a predetermined protocol to enable correlating the stimulation period with the physiological parameter; and a controller operative to:
- change a signal parameter of the first electrical signal to generate a second electrical signal;
- apply the second electrical signal to the neural structure, wherein the signal parameter is changed based upon the physiological parameter, based upon input from the external unit, or based upon the physiological parameter and the input from the external unit, wherein the signal parameter includes at least one of a pulse width, a frequency, a polarity, or an amplitude, and wherein the first and second electrical signals are applied to the neural structure to treat depression; and
- in response to the applied first and second electrical signals, determine a severity of the depression based on the sensed physiological parameter.

12. The implantable medical system of claim 11, wherein the communication unit is configured to receive data specifying the signal parameter from the external unit.

13. The implantable medical system of claim 11, wherein the communication unit is configured to send data indicating a status condition to the external unit.

14. The implantable medical system of claim 11, wherein the external unit comprises a computer system.

15. The implantable medical system of claim 11, further comprising at least three additional sensors operative to sense additional physiological parameters, wherein the sensor and the at least three additional sensors are configured to sense physiological parameters associated with at least four different organ systems of a body.

16. The implantable medical system of claim 11, wherein the sensor includes a filter unit operative to filter data associated with the sensed physiological parameter, and wherein the sensor is configured to be implanted in at least one of a spinal column, a brain stem, a brain, a cranial nerve, a neural tissue, or a gastro-intestinal tract of a patient's body.

17. The implantable medical system of claim 16, wherein the filter unit includes one of a band-pass filter, a high-pass filter, a low-pass filter, or any combination thereof.

18. The implantable medical system of claim 11, wherein the afferent nerve impulses are configured to effect neuronal activity of a brain of a patient resulting in changes in the physiological parameter.

\* \* \* \* \*